(12) United States Patent
Sage, Jr. et al.

(10) Patent No.: US 7,588,558 B2
(45) Date of Patent: Sep. 15, 2009

(54) LAMINATED SPRINKLER HYPODERMIC NEEDLE

(75) Inventors: Burton H. Sage, Jr., Carlsbad, CA (US); David Gillett, San Diego, CA (US)

(73) Assignee: Thera Fuse, Inc., San Diego, CA (US)

( * ) Notice: Subject to any disclaimer, the term of this patent is extended or adjusted under 35 U.S.C. 154(b) by 306 days.

(21) Appl. No.: 11/593,675

(22) Filed: Nov. 7, 2006

(65) Prior Publication Data

US 2007/0129691 A1 Jun. 7, 2007

Related U.S. Application Data (60) Provisional application No. 60/735,942, filed on Nov. 10, 2005.

(51) Int. Cl.
  *A61M 5/00* (2006.01)
  *A61K 9/22* (2006.01)
  *A61B 5/05* (2006.01)

(52) U.S. Cl. ............... 604/173; 600/347; 604/890.1

(58) Field of Classification Search ................ 604/173, 604/890.1; 435/287.2
See application file for complete search history.

(56) References Cited

U.S. PATENT DOCUMENTS

| | | | |
|---|---|---|---|
| 2006/0084942 A1* | 4/2006 | Kim et al. | 604/890.1 |
| 2006/0134448 A1* | 6/2006 | Daniel et al. | 428/596 |
| 2007/0027383 A1* | 2/2007 | Peyser et al. | 600/347 |
| 2007/0218372 A1* | 9/2007 | Zalevsky et al. | 430/5 |
| 2007/0233016 A1* | 10/2007 | Kuo et al. | 604/272 |
| 2008/0089637 A1* | 4/2008 | Farah | 385/14 |

* cited by examiner

*Primary Examiner*—Nicholas D Lucchesi
*Assistant Examiner*—Ian K Holloway (57) ABSTRACT

A laminated sprinkler needle for introduction of liquids into an animal and extraction of fluids from an animal comprising a substrate, a micromachined photoresist layer, and a microporous layer is described. The structure is of simple construction and fabrication and provides much higher flow rates than standard hollow cannula.

14 Claims, 8 Drawing Sheets

Figure 8

LAMINATED SPRINKLER HYPODERMIC NEEDLE

This application claims priority to and subject matter disclosed in provisional application No. 60/735,942, filed on Nov. 10, 2005; the content of this application being incorporated by reference herein in its entirety.

FIELD OF THE INVENTION

This invention relates to the introduction to the body or extraction of fluid from the body. Specifically, it relates to the configuration of a needle for that purpose and a method of manufacture for that needle.

BACKGROUND

Hypodermic needles have been used to introduce therapeutic medications to the body for over a century. Needles of a similar construction, that is, a tubular metallic cannula with a lumen running the axis of the needle is sharpened and attached to a syringe, are also used to extract blood and other fluid from the body. The use of these needles for these purposes has long been the method of last resort, especially for the injection of medications because of the pain associated with the forcing of the needle into the body. Over the years manufacturers of these hypodermic needles have learned that the smaller the diameter of the needle and the sharper the point of the needle, the more comfortable the injection would be. Today, it is common to inject medications with very fine needles such as those made by the Becton Dickinson Company of New Jersey.

However, there is a limit to the degree to which the diameter of these needles may be reduced. One limitation is established by the flow rate of the liquid along the cannula which is related to the fourth power of the diameter of the needle. As the diameter is reduced, the flow rate rapidly decreases. If a certain volume of fluid is to be injected and the diameter to be reduced, either the pressure used to move the fluid along the cannula or the time allotted for introducing the fluid will increase. Fluids such as insulin for the treatment of diabetes are usually injected in the home by the person with diabetes. Such individuals are unable to exert sufficient pressure to inject their insulin in a satisfactorily short period of time if the fineness of the needle, expressed in gauge, is finer than 31 G. At 31 G fineness, the injection, while being considerably more comfortable than 28 G and 29 G needles used in earlier years, is still sufficiently uncomfortable to be the number one reason why persons with diabetes strongly prefer to not be on insulin if at all possible. Other medical uses of hypodermic needles are also known to be painful. These uses include venipuncture for drawing blood, dialysis, and One way to increase the flow rate of a fluid passing through a cannula is to place openings along the side of the needle. Such needles, known as sprinkler needles are known in the art and are described, for example, by Gross in U.S. Pat. No. 6,261,272, incorporated herein in its entirely be reference. The additional openings on the side of the needle provide additional access to the tissue creating both a shorter path to the tissue, thereby reducing the distance the fluid has to travel and increasing the area of the access to the tissue thereby increasing the effective area of the outlet of the needle. These advantages exist both in the delivery of the fluid to the tissue and the extraction of fluid from the tissue. Sprinkler needles have the additional advantage of delivering the fluid to a larger volume of tissue thereby reducing the pressure needed to deliver the fluid and increasing the surface area of tissue exposed to the fluid thereby enhancing the absorption rate of the fluid by the body.

While sprinkler needles have a performance advantage over straight cannula needles, this performance advantage comes at a significantly higher manufacturing cost. The additional openings must be cut in the sides of the needle which takes more time and additional manufacturing setups, and these openings must further be deburred to make sure the pain of insertion is low. Hence there exists a need for improved hypodermic needles.

SUMMARY OF THE INVENTION

In one aspect of the invention, a photoresist material is layered on a support to both establish the flow channel for the laminated sprinkler needle and to adhere a microporous layer to the photoresist layer. The support layer may be made of any material suitable for sustaining the forces created during the penetration of the needle into skin. The support should also be capable of being sharpened to a very fine point to minimize trauma and pain during penetration of the skin. Suitable materials for the support layer include metals such as stainless steel and ceramics. The photoresist layer is one suitable for photolithography for creation of fluid flow pathways. For the purposes of this specification, photolithography will be defined as the process by which patterns are created in a photoresist material. Specifically, photolithography includes the steps of creating a mask comprising a desired pattern. Using the mask, the pattern is imaged onto the photoresist material either by direct contact with the photoresist material or using an optical imaging system. An energy beam is directed at the mask and impinges the photoresist material through selected portions of the mask thereby altering the properties of the photoresist material in such a way that portions of the photoresist may be selectively removed, usually by chemical etching, leaving unaffected the desired pattern in the material. If the photoresist material is a positive photoresist material, the irradiated portions of the photoresist material will be etched away. If the photoresist material is a negative photoresist material, the portions of the material not irradiated, that is the irradiating energy is blocked by the mask, will be etched away.

An additional property of the photoresist material is that it should be patternable by photolithography in a partially hardened state. In this way a microporous membrane may be adhered to the upper surface of the patterned photoresist by contacting the microporous membrane to the upper surface and treating the photoresist to completely harden. The treatment to completely harden or cure the photoresist causes the microporous membrane to firmly adhere to the photoresist layer.

In a second aspect of the invention, a second photoresist layer is used to create the microporous membrane. In this second aspect, two support layers are used, and the photoresist is layered on the support layer and treated such that the photoresist layer adheres to the support layer. In one embodiment of the invention, the photoresist layer is heated to adhere it to the support layer. One of the support and photoresist layers is photolithographically processed to create at least one flow channel. The other support and photoresist layer is processed photolithographically to create a plurality of pores such that the pores penetrate through the photoresist layer to the support layer. After photolithographically processing the two photoresist layers, the tops of the photoresist layers are contacted and pressed together and heated causing the two subsystems to permanently attach. In a final step, the second support layer is released such that the remaining system comprises three layers—the first support layer, the first photoresist layer containing the flow channel, and the photoresist layer containing the plurality of pores.

DETAILED DESCRIPTION

Figure 1:
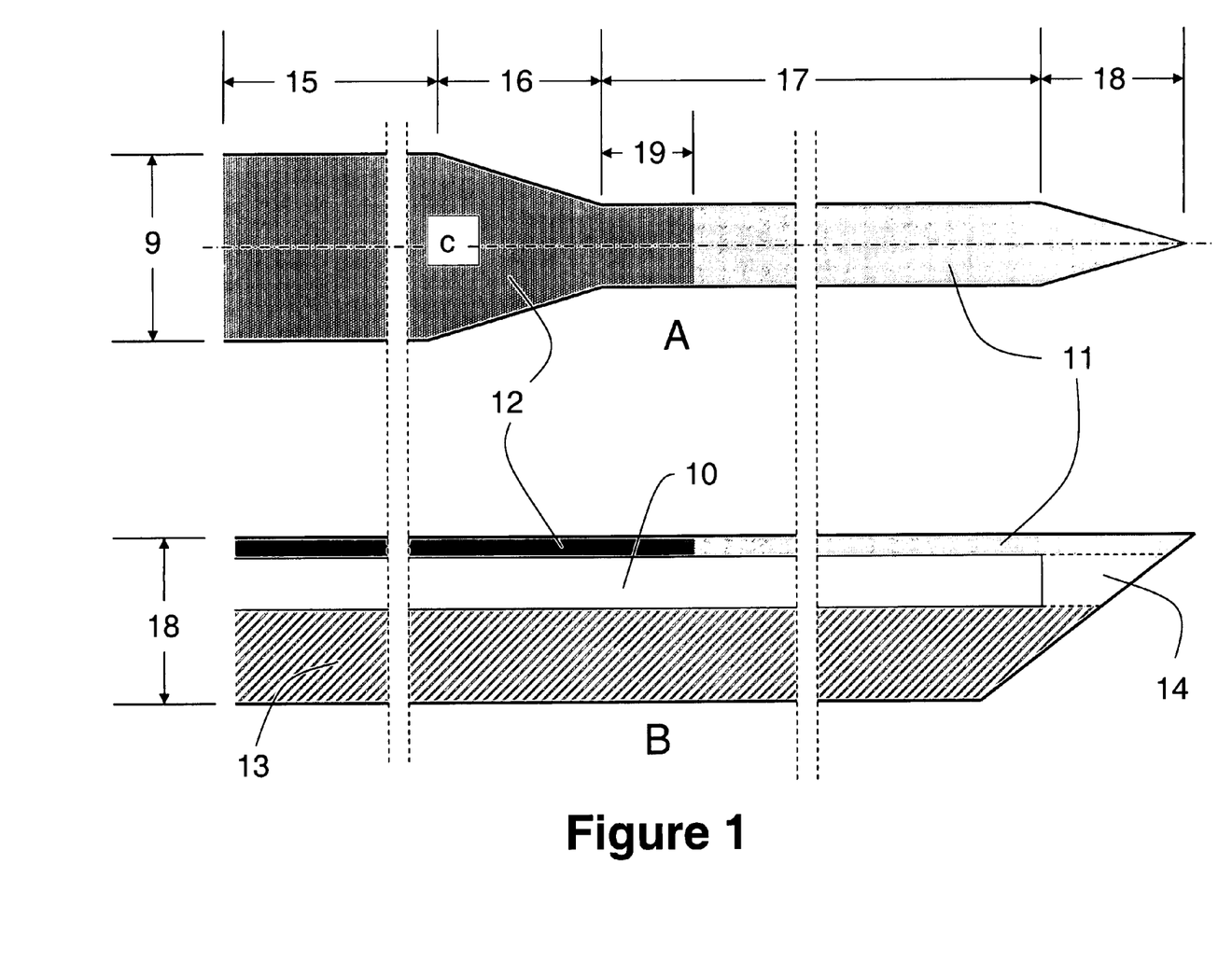
FIG. 1 shows two views of a sprinkler needle of the first aspect of the invention.

FIG. 1 shows two views of one embodiment of a sprinkler needle of this invention. FIG. 1A is a plan view of the needle—the vertical hash marks break the overall length of the needle so that the key portions of the needle may be shown. The overall length of the needle is much greater than shown in any of FIGS. 1 through 5. In FIG. 1, there is a hub region shown as dimension 15. This is the portion of the needle that would allow the needle to be mated to a fluid delivery device such as a syringe or pen. Dimension 16 is a region of width reduction so that the portion of the needle that actually enters skin is as thin as possible in order that the pain of needle insertion is as low as possible. Dimension 17 denotes the length of the shaft of the needle. Dimension 18 denotes the portion of the needle that is pointed. Dimension 9 denotes the width of the needle in the hub region. The width of the portion of the needle that penetrates skin is typically half that of dimension 9, but may be greater or smaller depending on the actual use of the needle. While in no way limiting the scope of the invention, typical dimension of the needle would be a hub length 15 of about 5 mm, a neck down region of length 16 of about 3 mm and a shaft length 17 of about 8 mm and a point length 18 of about 1 mm. Also shown is length 19 which is a region beneath the skin when the needle has penetrated skin through which the liquid may not leave the needle. A typical dimension of length 19 is 3 mm so that fluid leaving the needle along the shaft further down the shaft from length 19 will not seep out of the skin along the shaft of the needle. Also shown in FIG. 1 is needle thickness dimension 18. Again, in no way limiting the scope of the invention, a typical width 9 of the needle may be 1.0 mm narrowing down to 0.3 mm along shaft 17 and a typical thickness 18 of the needle may also be 0.3 mm.

In FIG. 1A there is a centerline denoted by the letter c. FIG. 1B is the view of the needle that would be seen if the needle were cut lengthwise along centerline c. Shown in FIG. 1B is lumen 10 which runs the entire length of the needle. Shown also in FIG. 1B are the three layers that comprise the needle. The bottom layer 13 is a support or structural layer. It may be made of any appropriate material such as a metal or ceramic that resists fracture under a bending stress. Support layer 13 also provides an upper surface that photoresist layer 14 will adhere to. Photoresist layer 14 is shown in greater detail in FIG. 2. The upper layer has two portions—portion 11 covering mainly the shaft of the needle and is microporous so that liquid moving down lumen 10 may leave the needle into the skin when the needle is inserted into skin. The second portion 12 of the upper layer is not microporous and liquid flowing in lumen 10 may not leave the lumen through portion 12 of the upper layer.

Figure 2:
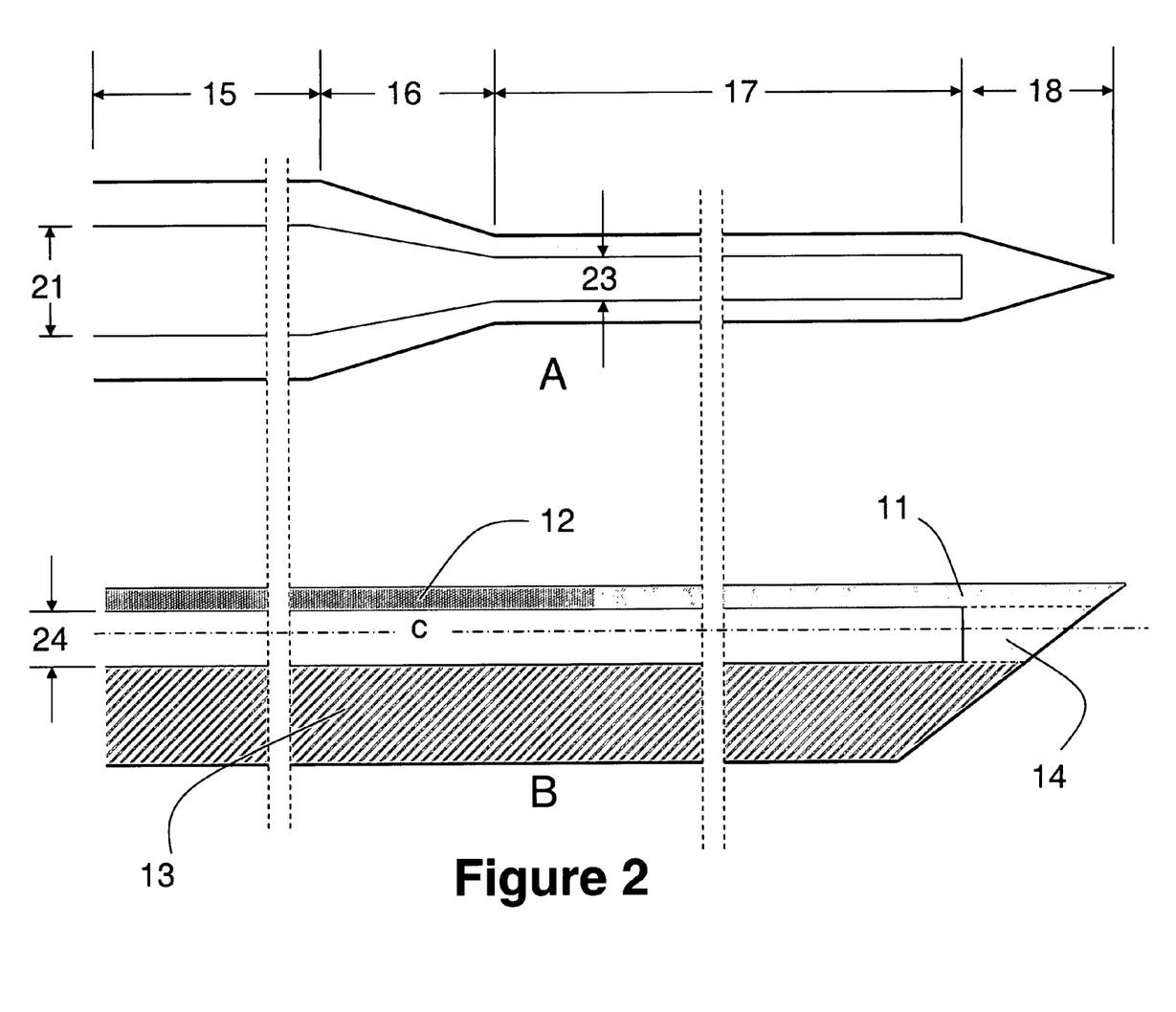
FIG. 2 shows two additional views of the sprinkler needle of FIG. 1

FIG. 2 shows another view of the sprinkler needle shown in FIG. 1. FIG. 2B is the same as FIG. 1B with the exception that centerline c is a horizontal cut through the needle and FIG. 2A is a view of the needle as seen if the needle was cut along this line and the upper portion removed. In general, FIG. 1A shows the pattern of the photoresist layer 14 that actually forms the lumen of the needle. In the hub region of the needle, depicted by dimension 15, the lumen has dimension 21. This lumen narrows to dimension 23 in the neck down region of the needle denoted by dimension 16. Typical dimensions, which in no way limit the scope of the invention, are 0.5 mm for dimension 21 and 0.1 mm for dimension 23. Shown in FIG. 2B is dimension 24 which is the depth of the lumen of the needle. A typical dimension for this depth, which in no way limits the scope of the invention, would be 0.1 mm.

The upper layer of the needle is a microporous membrane with two regions 12 and 11. As in FIG. 1, region 12 denotes a region of the membrane where the pores have been filled so that fluid may not enter or leave the needle along this portion of the needle. Region 11 denotes the portion of the membrane where the pores have not been filled so that fluid may readily enter of leave the lumen of the needle along this portion of the length of the needle.

In FIGS. 1 and 2, layer 14 is a photoresist material that is applied to the upper surface of support 13. The photoresist material is typically a negative photoresist layer and may be SU-8 or any other similar material. This photoresist layer is patterned by a photolithographic method so that multiple copies of the needle may be made at the same time. After application to the upper surface and patterning by photolithographic methods well known in the art, the support and layer is heated to partially harden the photoresist layer. The photoresist layer is then placed in an etchant to remove the photoresist layer to form the needle lumens. After drying, the microporous membrane is placed on the upper surface of the photoresist layer and the whole assembly baked to permanently adhere the membrane to the photoresist layer. In a final step, a mask is placed over the baked assembly that shields the portions 11 of the needle and the pores of portions 12 of the needle and all other areas of the assembly are filled. Once this pore filling step is complete, the individual needles are created. This needle creation process may be done with a stamping process with a die appropriately shaped to cut out the individual needles or the needles may be cut out using a laser or similar cutter.

Figure 3:
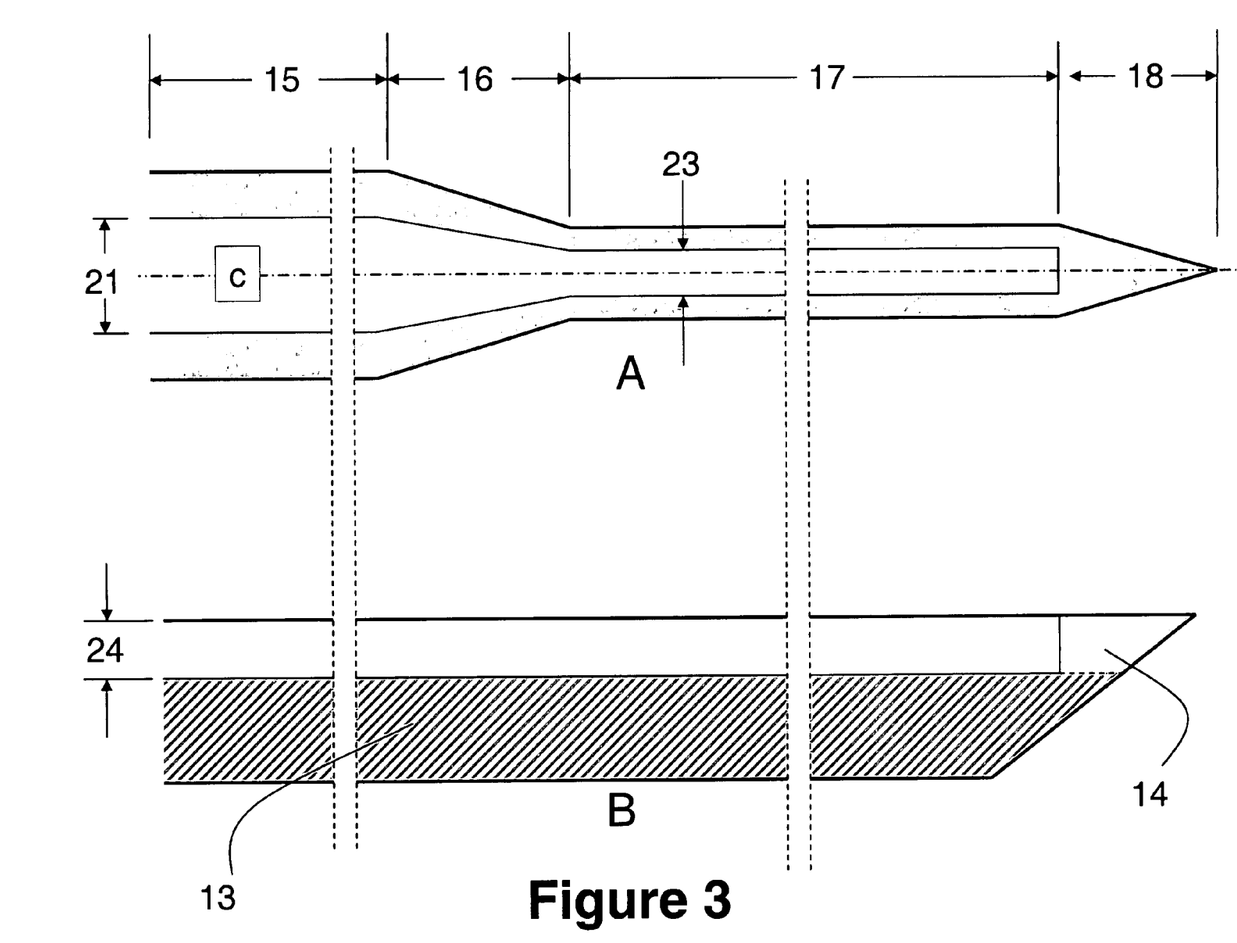
FIG. 3 shows a first support layer of a needle of the second aspect of the invention
Figure 4:
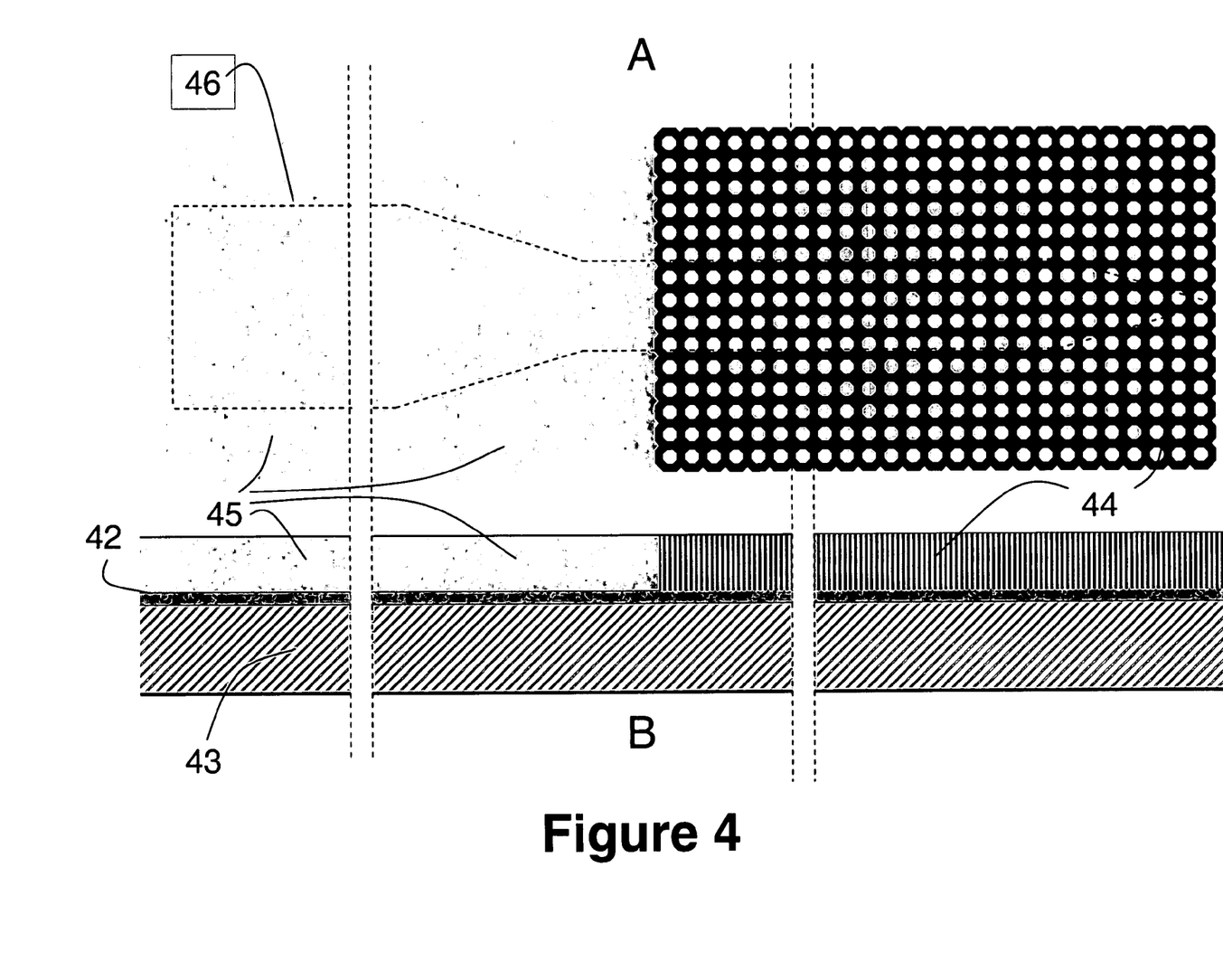
FIG. 4 shows a second support layer of a needle of the second aspect of the invention
Figure 5:
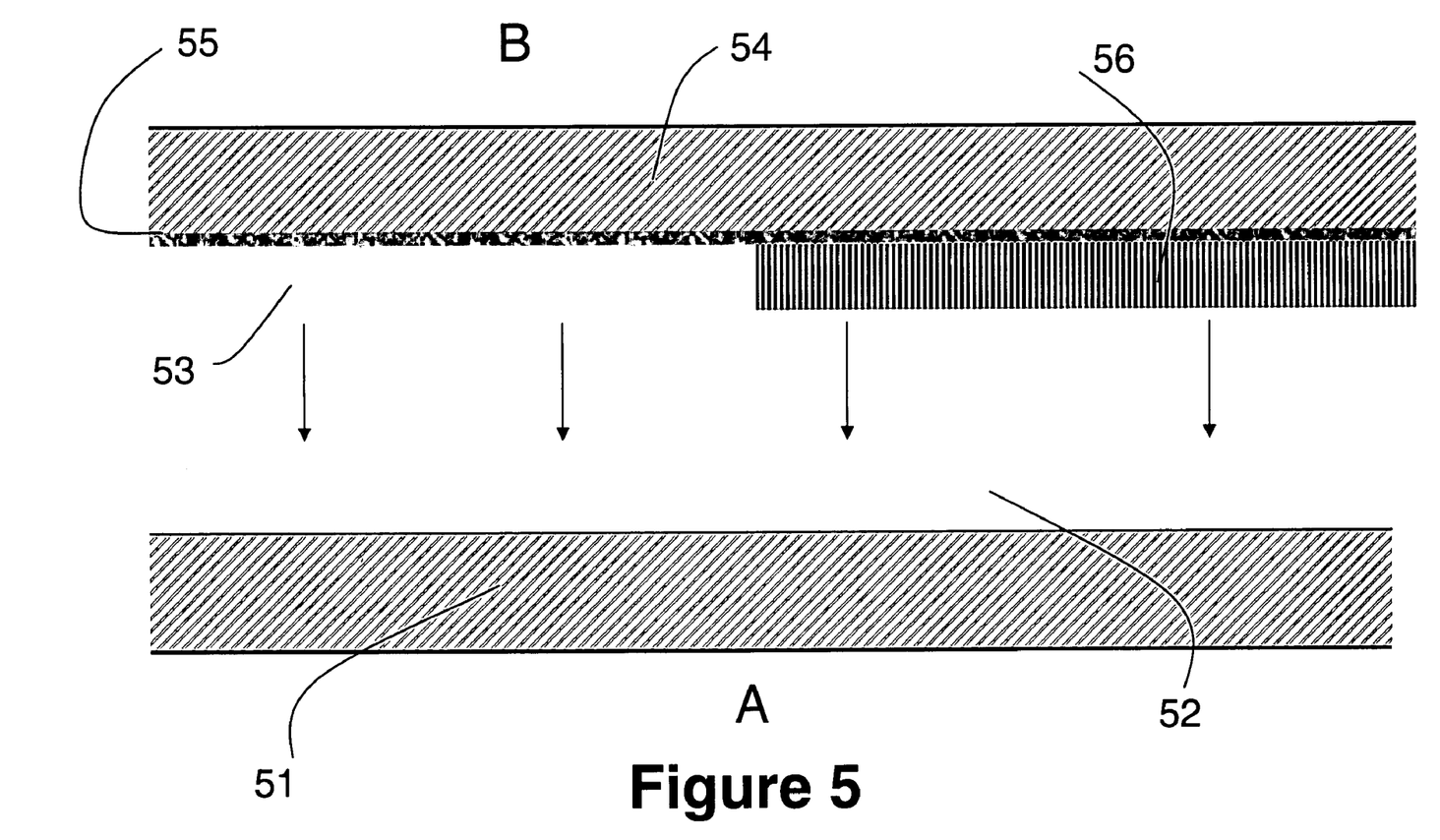
FIG. 5 shows the support layers of FIG. 3 and FIG. 4 being contacted.

FIGS. 3, 4 and 5 depict an alternate sprinkler needle construction. FIG. 3 is similar in many ways to FIG. 2 with the main exception that the microporous layer with regions 11 and 12 is not present. Only support layer 13 and photoresist layer 14 are included. FIG. 3A shows a plan view of the sprinkler needle, dimensioned similarly to the needle shown in FIG. 1. A centerline, denoted by the small letter c is also shown in FIG. 3A. FIG. 3B shows a view of the needle along centerline c. Here support 13 and photoresist layer 14 are shown clearly. The portion of the needle shown in FIG. 3 is a "bottom" portion of the needle and in a subsequent process will be mated with an "upper" portion of the needle.

FIG. 4 shows the "upper" portion of the needle although in this view it is still attached to a support used in its construction. FIG. 3A shows the "upper" portion of the needle in outline by dashed line 46. As in the case of the needle construction method shown in FIGS. 1 and 2, the "upper" portion of the needle using the construction method shown in FIGS. 3, 4, and 5 is made using support layer 43 in FIG. 3. In the making of the "upper" portion of the needle, release layer 42 is placed on support layer 43. The method application of release layer 42 may be by spinning as is customary in placing photoresist layers on supports. Photoresist layer 45 as shown in FIG. 4 is then applied to release layer 42. Again, the process of application of photoresist layer 45 may be by spinning as is well known in the semiconductor industry. Photoresist layer 45 in FIG. 4 is shown as unprocessed photoresist layer 45 and processed photoresist layer 44. In fact, the layer as applied is one contiguous layer as shown as 45. After the next step of performing photolithography there will be regions where the layer exists as a solid contiguous layer and other regions 44 where pores have been created in the layer. Once photoresist layer 45 has been applied, it is patterned photolithographically as is well known in the semiconductor industry into regions as shown in FIG. 4A. The patterns are rectangular as shown in FIG. 4A and each rectangle pair consists of a contiguous region 45 and a microporous region 44, the pair of regions essentially covering one sprinkler needle as shown. Over the entire area of support 43 there may be multiple copies of the pair of regions 45 and 44, each representing the area of one needle.

The next step of mating the "bottom" portion of the needle as shown in FIG. 3A with the "upper" portion of the needle as shown in FIG. 4A is depicted in FIG. 5. As described above, prior to mating of the "bottom" portion and the "upper" portion, the two photoresist layers 14 in FIGS. 3B and 45 and 44 in FIG. 4 will have been partially heated and patterned and etched to created the physical pattern. The supports comprising the needle bottoms and tops will then be aligned so that the needle outlines shown in FIGS. 3 and 4 coincide. The aligned supports will then be mated and baked to cause the two photoresist layer to permanently adhere. After baking, the mated structure will be placed in a bath to release support 54 by etching away release layer 55 as shown in FIG. 5. The result is support 51 shown in FIG. 5 comprising multiple sprinkler needles. The final step will be cutting out the multiple needles from support 51. This may be done using a die with multiple copies of the shape of the desired needle or may be done with laser cutting or other similar methods used to extract the multiple copies of an item contained on a substrate as is well known in the semiconductor industry.

Figure 6:
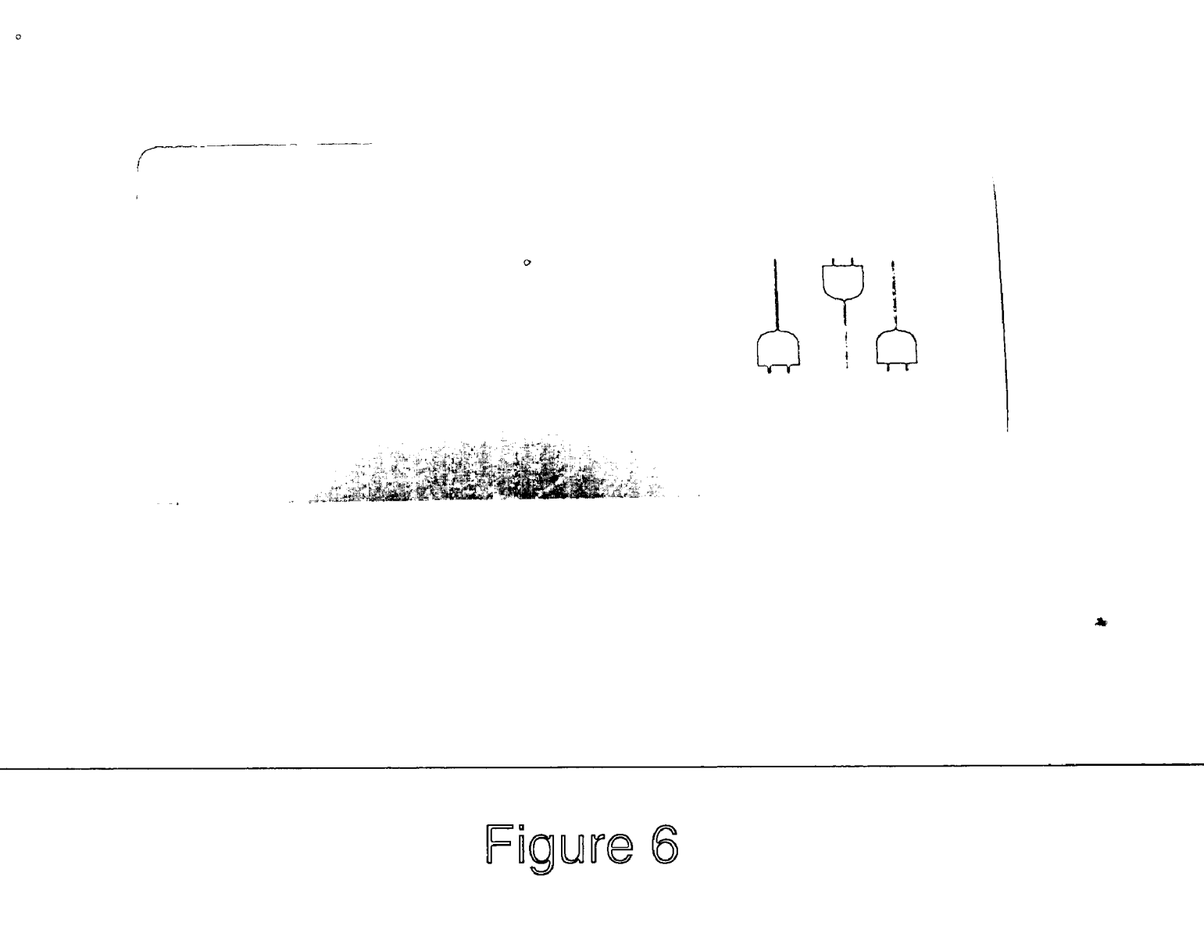
FIG. 6 is a photograph of several prototypes before laser cutting.
Figure 7:
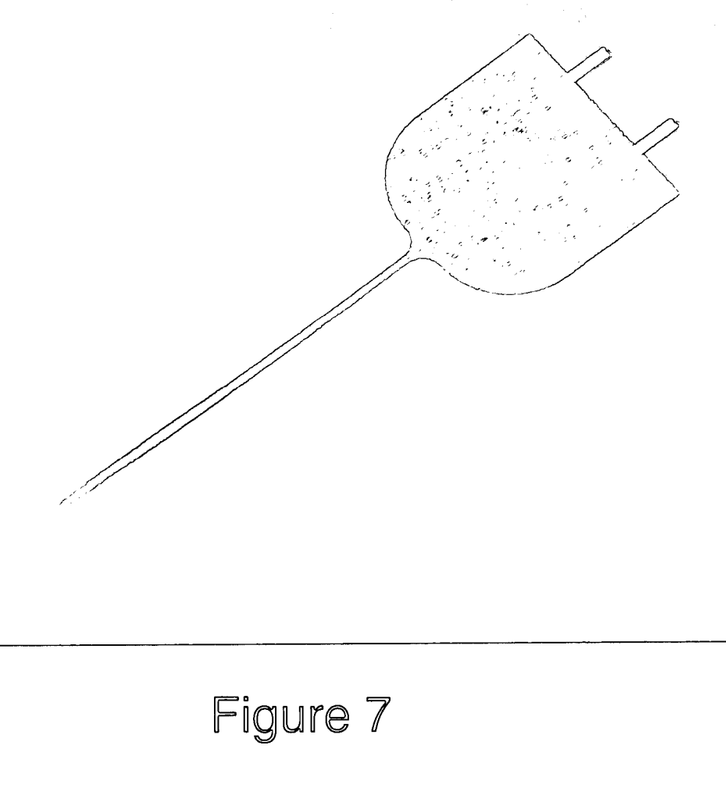
FIG. 7 is a photograph of a laser cut prototype of the first aspect of the invention.
Figure 8:
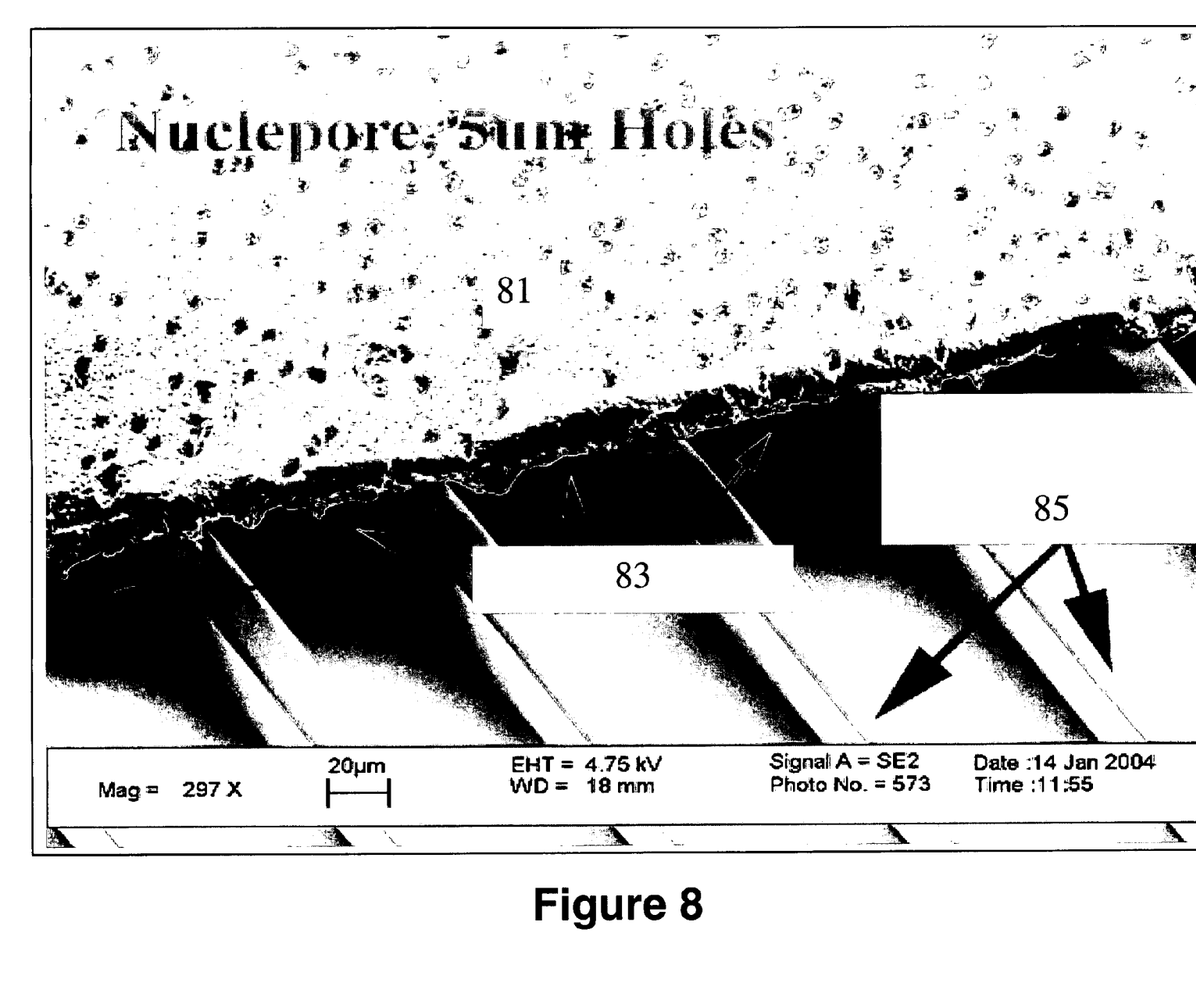
FIG. 8 is an SEM of a prototype lamination.

FIGS. 1 and 2 and FIGS. 3, 4, and 5 describe two alternative methods for making the sprinkler needles of the invention. Other methods of making the needles are possible. FIG. 6 is a photograph of a support with multiple copies of the needle ready for the final step of cutting the needles from the support. FIG. 7 is a photograph of a single needle of the invention after being cut out from the support shown in FIG. 6. FIG. 8 is a photomicrograph of the process used to make the needle of the invention that is described in conjunction with FIGS. 1 and 2. In FIG. 8, microporous filter 81 is adhered to photoresist 85. Photoresist 85 has been patterned using photolithographic processes to create channels 83. Photoresist layer 85 is adhered to the support as shown.

It should be clear that the sprinkler needle of the invention may be used either to deliver fluids to tissue. The needle of the invention would be used in combination with a syringe. If the needle is hubbed to the syringe and the syringe filled with fluid and the needle inserted into tissue, when the plunger of the syringe is pressed, the fluid will pass out of the syringe, into the needle and through the pores of the needle into tissue. Likewise, if the needle is hubbed to the syringe and the plunger is pressed all the way into the syringe barrel and the needle placed into tissue, pulling back on the plunger will cause fluid from tissue to enter the needle through the pores and move up the lumen of the needle into the barrel of the syringe. By virtue of the larger passageway between the tissue and the lumen of the needle as represented by the pores as compared to a normal needle with only an opening at the end of the cannula, fluid more easily moves into or out of the needle and hence into or out of tissue.

We claim:

1. A device for penetrating the skin of a body for delivering fluids to the body or extracting fluids from the body comprising three layers, the three layers in order from bottom to top being a first layer for providing support, a second photoresist layer adhered to the bottom layer comprising a fluid flow path and a microporous third layer adhered to the second layer enclosing the fluid flow path wherein
   a) the device is elongate with a proximal end and a distal end, and
   b) the device comprises an opening to the fluid flow path at the proximal end of the device, and
   c) the microporous third layer comprises a multiplicity of fluid openings to the fluid flow path only near the distal end of the device.

2. The device of claim one wherein the first layer is a metal.

3. The device of claim 2 wherein the metal is stainless steel.

4. The device of claim 1 wherein the photoresist layer comprises a negative photoresist.

5. The device of claim 4 wherein the negative photoresist is SU-8.

6. The device of claim 1 wherein the microporous third layer is a track-etch membrane.

7. The device of claim 1 wherein the microporous third layer is comprised of a negative photoresist.

8. The device of claim 7 wherein the negative photoresist is SU-8.

9. A method of manufacturing the device of claim 1 comprising the steps of
   a) providing the first support layer with an upper surface,
   b) adhering the photoresist layer to the upper surface of the first support layer by applying the photoresist material to the upper surface of the first support layer and heating such that the photoresist material is partially hardened creating a new upper surface,
   c) photolithographically creating at least one flow channel in the partially hardened photoresist layer,
   d) placing a semipermeable membrane in contact with the new upper surface, and
   e) heating the product of step d) to adhere the semipermeable membrane to the photoresist layer and to permanently harden the photoresist layer.

10. The method of claim 9 wherein the photoresist is a negative photoresist.

11. The method of claim 10 wherein the negative photoresist is SU-8.

12. The method of claim 8 further comprising the steps of creating a die patterned with multiple copies of the external device configuration and using the die to stamp out multiple copies of the device.

13. The method of claim 8 further comprising the steps of programming a laser cutter with the external device configuration and using the laser cutter to cut out multiple copies of the device from the support.

14. A method of manufacturing the device of claim 1 comprising the steps of
   a) providing first and second support layers each with an upper surface, b) adhering a photoresist layer to the upper surface of each support layer by applying the photoresist material to the upper surface of each support layer and treating the photoresist material such that the photoresist material is partially hardened creating a new upper surface,
c) photolithographically creating at least one flow channel in the partially hardened photoresist layer on the first support layer,
d) photolithographically creating a pattern of depressions in the partially hardened photoresist layer on the second support layer such that the depressions penetrate through the photoresist layer to the upper surface of the second support layer,
e) contacting the new upper surfaces of each support layer and heating thereby causing the two new upper surfaces to adhere, and
f) releasing the second support surface from the product created in step e).

* * * * *